United States Patent [19]

Young et al.

[11] Patent Number: 5,046,490
[45] Date of Patent: Sep. 10, 1991

[54] ORTHOPAEDIC BRACE AND MOTION CONTROL MECHANISM THEREFOR

[75] Inventors: David E. Young, Watlington; Kenneth P. Davis, Hillington, both of England

[73] Assignee: Protectair Limited, Abingdon, England

[21] Appl. No.: 533,119

[22] Filed: Jun. 4, 1990

[30] Foreign Application Priority Data

Jun. 15, 1989 [GB] United Kingdom ................. 8913759

[51] Int. Cl.⁵ .............................................. A61F 5/04
[52] U.S. Cl. .................................. 128/87 B; 128/76 R
[58] Field of Search ............... 128/76 R, 80 R, 80 A, 128/80 C, 80 F, 80 H, 84 R, 84 A, 84 B, 84 C, 83.5, 88, 87 B, 166, 75, 25 R

[56] References Cited

U.S. PATENT DOCUMENTS

| 2,735,424 | 2/1956 | Benjamin | 128/87 |
|---|---|---|---|
| 2,807,260 | 9/1957 | Teufel | 128/87 |
| 2,820,455 | 1/1958 | Hall | 128/87 |
| 4,099,525 | 7/1978 | McCarthy | 128/87 R |
| 4,716,889 | 1/1988 | Saringer | 128/25 R |
| 4,771,768 | 9/1988 | Crispin | 128/88 |
| 4,856,500 | 8/1989 | Spademan | 128/88 X |
| 4,919,118 | 4/1990 | Morris | 128/88 |
| 4,936,295 | 6/1990 | Crane | 128/80 H |

FOREIGN PATENT DOCUMENTS 1503797 12/1987 U.S.S.R. .
1314973 4/1973 United Kingdom .
1457180 12/1976 United Kingdom .

OTHER PUBLICATIONS

European Patent Appl. 0359523, published 3/21/90.

Primary Examiner—Richard J. Apley
Assistant Examiner—Jennifer L. Doyle
Attorney, Agent, or Firm—Tilton, Fallon, Lungmus

[57] ABSTRACT

An orthopaedic brace having an adjustable control mechanism for controlling in a continuously variable manner the limits of pivotal movement of a body support member. The mechanism includes a threaded guide rod with a longitudinal slot, a collar slidably carried by the rod and equipped with an insert element projecting into the slot for preventing relative rotation of the collar and rod, and a pair of stop members disposed on opposite sides of the collar for controlling the extent of the collar's sliding movement. At least one of the stop members is in the form of a nut threadedly mounted upon the rod.

6 Claims, 1 Drawing Sheet

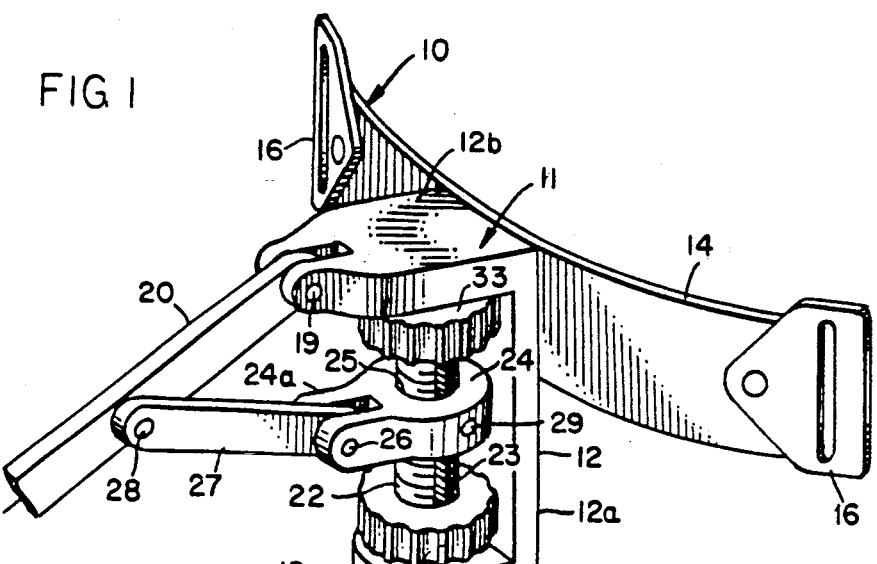
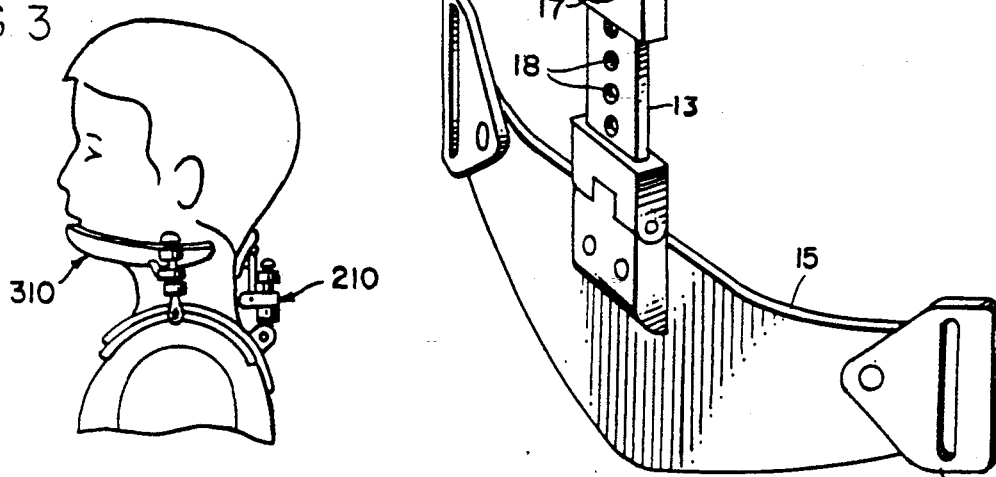
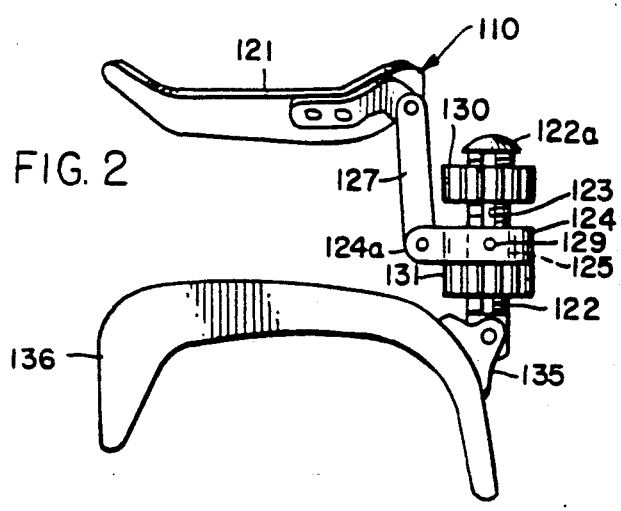
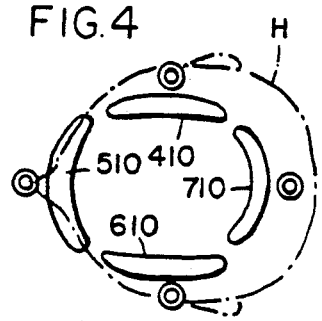

ORTHOPAEDIC BRACE AND MOTION CONTROL MECHANISM THEREFOR

This invention relates to orthopaedic braces in which a limited range of movement of a limb or other body part may be permitted.

Many orthopaedic conditions require bracing to augment the structure or function of a limb or joint. In some chronic conditions, or where rehabilitation after surgery is well advanced, it may be desirable to allow the joint to move through a preselected range of motion. Such devices must necessarily be designed with architecture which is appropriate to the type of joint and its scope for motion. In this way the dual functions of the brace in augmenting support and accommodating or facilitating motion can be achieved.

For instance, in the knee, the main motion is flexion and extension. A limb orthosis used about the knee would generally have rigid medial and lateral support members above and below the joint and a hinge mechanism bridging such members. The hinge, like the joint, would be built only to accommodate flexion/extension motion at the knee and any range of motion restricting mechanism incorporated therein would act either to contain or de-restrict such motion.

Joints with normal movement in additional planes, such as the shoulder, pose different problems. In this case flexion/extension, abduction/adduction and rotation are all possible over a wide range. On the other hand, the joint is not weight bearing in the same sense that the knee or hip are weight bearing.

Until recently, orthotic design for the lower limb has been much more intensive and wide ranging than for the upper limb. The reasons are fairly obvious in that structural or dynamic failure of the hip or knee directly impairs or prevents mobility. Similar failure in the upper limb leads to less disabling sequelae. Notwithstanding this, there are numerous injuries due to trauma and overuse which can, in damaging the upper limb, markedly restrict or incapacitate the sufferer. The damaged shoulder can make driving or writing impossible and eating difficult.

Resolution of shoulder injuries by arthroscopic surgical techniques has grown apace over the last few years and this has led to increased expectations by the public, especially in the United States where in 1989 the shoulder is quoted by the American Academy of Orthopaedic Surgeons as constituting 14% of all consultations.

The present invention is concerned with an orthopaedic brace equipped with means for selectively and adjustably controlling the range of motion in a joint in at least one plane of motion in a continuously variable manner over at least a clinically useful range. Theoretically, the motion control mechanism can be used for any of a wide variety of included angle braces; however, the principal value is obtained where the structures to be braced are normally positioned or move between positions not much more than 90 degrees apart. Examples are the shoulder (control of abduction/adduction), hips (control of abduction/adduction in conditions such as Perthes disease and congenital dislocation), the ankle (control of dorsiflexion/plantarflexion), and the head (control of flexion/extension of the neck in the presence of damaged cervical spine and/or associated structures).

Briefly, the motion control mechanism comprises a threaded guide rod and a collar with an opening that receives the rod for longitudinal sliding movement therealong. Stop members are provided along the rod on opposite sides of the collar for limiting the extent of longitudinal sliding movement of the collar. At least one (and preferably both) of the stop members takes the form of an adjustment nut threaded upon the rod for selectively and variably controlling the extent of sliding movement of the collar along the rod. In preferred embodiments, the threaded rod has a longitudinal groove and the collar is provided with antirotation means for preventing relative rotational movement of the collar and rod.

The rod is secured to mounting means adapted for connection to a patient so that the rod is immobilized against at least longitudinal movement with respect to a first part of a patient's body. The complete orthopaedic device also includes support means for engaging a second body part to be braced in relation to the first body part. A connecting member or arm joins the support means to the collar so that protected movement of the braced body part is translated into longitudinal movement of the collar along the threaded shaft. By adjusting the stop nuts on opposite sides of the collar, the position and range of movement of the support means for the second body part may be effectively adjusted in a continuously variable (i.e., non-incremental) manner.

DRAWINGS

FIG. 1 is a perspective view of an orthopaedic shoulder brace embodying the motion control mechanism of the present invention.

FIG. 2 is a side elevational view of a cervical head brace embodying the invention.

FIG. 3 is an elevational view showing a cervical brace and revealing two of the motion control mechanisms of that brace.

FIG. 4 is a schematic top view of a cervical brace having an arrangement of four motion control devices as they might be used in treating diseases or injuries of the cervical spine.

DETAILED DESCRIPTION OF PREFERRED EMBODIMENTS

Referring to FIG. 1, the numeral 10 generally designates an orthopaedic shoulder brace having a hinge mechanism 11 for controlling abduction and adduction. The hinge mechanism includes mounting means in the form of a hinge body 12, an extension bar 13 adjustably connected to the body 12, and plates or straps 14, 15 connected to the hinge body and extension bar, respectively. The plates 14, 15 may be formed of semirigid plastics material equipped at their ends with slotted fittings 16 for receiving straps (not shown) to attach the brace to a first body part (i.e., trunk) of a patient. When the brace is properly fitted or mounted upon a patient, hinge body 11 should be located directly below the shoulder requiring treatment.

Adjustment of the brace by extension or retraction of extension bar 13 may be achieved in the manner disclosed in co-pending UK patent application 8821360.8. As disclosed in greater detail therein, a removable peg or pin 17 may be extended through any of a series of holes 18 to fix bar 13 and plates 14, 15 in positions that meet the requirements for a given patient.

Hinge body 12 has an upstanding intermediate portion 12a and a pair of spaced, integral end portions 12b and 12c. The upper end portion 12b is in the form of a yoke and is pivotally connected by pin 19 to one end of arm 20. As indicated diagramatically in FIG. 1, arm 20 is one component of support means 21 upon which a patient's arm would be supported. Movement of the support arm 20 about the axis of pin 19 therefore results in abduction/adduction of the patient's upper limb.

A threaded guide rod 22 spans the end portions 12b and 12c of hinge body 12 and has its ends securely fixed to the end portions of that body. A slot or channel 23 extends the length of the threaded rod and a collar 24, having an opening 25, is longitudinally slidable along rod 22. The collar has a yoke extension 24a that is pivotally connected by pin 26 to one end of a connecting member or link 27. The opposite end of the link is connected by pin 28 to support arm 20. Upward and downward pivotal movement of the support arm (and the support means 21 of which it is a part) is therefore accompanied by upward and downward sliding movement of collar 24 along threaded rod or shaft 22.

In the embodiment illustrated, means are provided for preventing independent relative rotation of collar 24 upon threaded guide rod 22. Such means includes slot 23 in rod 22 and radial pin or insert element 29 carried by collar 24. The pin protrudes into the slot and prevents relative rotation of the parts.

The extent of sliding movement of collar 24 along threaded rod 22 is controlled by adjustable stop means in the form of upper (first) and lower (second) adjustment nuts 30 and 31 threadedly carried by the rod on opposite sides of the collar. It is believed apparent that by rotating the nuts into contact with opposite sides of collar 24, the angle of support arm 20 may be set at any desired angle over a clinically useful range. Nut 30 controls the extent of abduction and nut 31 the extent of adduction so that, depending on the patient's condition, the limits of abduction, or adduction, or both, may be effectively controlled in a continuously variable (i.e., non-incremental) manner.

FIG. 2 depicts a similar motion control mechanism used for a head/neck brace 110. As in the first embodiment, a collar 124 has an opening 125 that slidably receives threaded guide rod 122. The collar has a yoke portion 124a pivotally joined to one end of a connecting member or link 127. The other end of member 127 is joined to support means 121 which, in the embodiment illustrated, is configured to engage and support the lower portion of a wearer's head.

The lower end of threaded guide rod 122 is connected by fitting 135 to mounting means in the form of a shoulder halter 136.

A slot 123 extends the length of threaded rod 122 and receives the inner end of a radially-extending pin or insert element 129 carried by collar 124. Adjustment nuts 130 and 131 are threaded upon rod 122 and are disposed above and below (i.e., on opposite sides of) the collar 124 to control the extent of longitudinal sliding movement of the collar on the guide rod. Preferably, the rod is provided with an enlarged head 122a for preventing accidental removal of nut 130.

In the embodiments described, pairs of adjustment nuts 30, 31 and 130, 131 are provided for adjustably controlling both upward movement and downward movement of the collars. It is to be understood that if adjustable control in only one direction is necessary, then one of the stop members of each pair may be fixed in relation to the rod.

It is also to be understood that a number of devices embodying the invention may be used in combination. For example, FIG. 3 depicts the positions of two motion control devices 210 and 310, each of which has a motion control adjustment mechanism as already described. The combination of two such braces 210 and 310 controls the movement of head in two directions at 90 degrees to one another. FIG. 4 diagramatically illustrates in plan view how four such braces 410-710, each having the motion control mechanism described, might be used for even more complete support of a patient's head H. By means of such arrangement, motion of the head and cervical spine can be limited or progressively de-restricted in any direction.

We claim:

1. An orthopaedic brace comprising a threaded guide rod; mounted means adapted for supporting said rod against at least longitudinal movement with respect to a first part of a patient's body; a collar having an opening receiving said rod for longitudinal sliding movement therealong; support means adapted for engaging a second body part to be braced with respect to said first part; a connecting member connecting said support means to said collar; first and second stoop means for limiting the extent of longitudinal sliding movement of said collar along said rod; at least one of said first and second stop means comprising an adjustment nut threadedly receiving said rod for selectively and variably controlling the extent of sliding movement of said collar along said rod; and antirotation means provided by said brace for preventing rotation of said collar upon said rod.

2. The brace of claim 1 in which said antirotation means are provided by said collar and said rod.

3. The brace of claim 2 in which said antirotation means comprises a slot extending longitudinally along said rod and an insert element provided by said collar and slidably received in said slot.

4. The brace of claim 1 which said collar includes a yoke portion projecting laterally away from said rod; and pivot means pivotally connecting said yoke portion to said connecting member.

5. The brace of claim 1 in which said mounting means includes a hinge body having an intermediate portion and a pair of spaced, outwardly-projecting end portions; said end portions engaging and supporting said threaded rod.

6. The brace of claim 1 in which said support means includes a support arm having one end pivotally connected to one of said end portions of said body; said support arm and said connecting member being pivotally connected together for pivotal movement in the same plane.

* * * * *